(12) United States Patent
Lo

(10) Patent No.: US 7,042,647 B2
(45) Date of Patent: May 9, 2006

(54) SCANNING OPTICAL SYSTEM

(75) Inventor: William K. Lo, San Jose, CA (US)

(73) Assignee: Credence Systems Corporation, Milpitas, CA (US)

( * ) Notice: Subject to any disclaimer, the term of this patent is extended or adjusted under 35 U.S.C. 154(b) by 180 days.

(21) Appl. No.: 10/677,587

(22) Filed: Oct. 2, 2003

(65) Prior Publication Data

US 2005/0073675 A1    Apr. 7, 2005

(51) Int. Cl.
*G02B 3/00*    (2006.01)
*G02B 7/02*    (2006.01)
*H01L 3/14*    (2006.01)

(52) U.S. Cl. .................. 359/652; 250/216; 250/234; 250/227.11; 359/664

(58) Field of Classification Search .. 356/237.1–237.5; 250/216, 234, 227.11, 306, 307; 359/656, 359/661, 368, 785, 652, 664
See application file for complete search history.

(56) References Cited

U.S. PATENT DOCUMENTS

| | | | | |
|---|---|---|---|---|
| 3,013,467 A | | 12/1961 | Minski | ....................... 356/432 |
| 5,208,648 A | * | 5/1993 | Batchelder et al. | ....... 356/237.1 |
| 5,939,709 A | * | 8/1999 | Ghislain et al. | ............. 250/216 |
| 6,317,276 B1 | * | 11/2001 | Braat | .......................... 359/785 |
| 6,441,359 B1 | * | 8/2002 | Cozier et al. | ................ 250/216 |
| 6,462,814 B1 | * | 10/2002 | Lo | ........................... 356/237.2 |
| 6,568,594 B1 | * | 5/2003 | Hendriks et al. | ............ 235/454 |
| 6,778,327 B1 | * | 8/2004 | Pakdaman et al. | ........... 359/656 |
| 6,841,096 B1 | * | 1/2005 | Quake et al. | ................. 264/2.5 |
| 6,856,712 B1 | * | 2/2005 | Fauver et al. | .................. 385/12 |

OTHER PUBLICATIONS

C.J.R. Sheppard and D.M. Shotton, *Confocal Laser Scanning Microscopy*, Royal Microscopical Society Microscopy Handbooks, Bios Scientific Publishers LTD, 1997, pp. 6-13.

* cited by examiner

*Primary Examiner*—Samuel A. Turner
*Assistant Examiner*—Sang H. Nguyen
(74) *Attorney, Agent, or Firm*—Deborah W. Wenocur

(57) ABSTRACT

A scanned optical system for use in optical probing applications provides a large Field of View (FOV) for objective lenses having high Numerical Aperture (NA), such as Solid Immersion Lenses (SIL's). This enables high resolution imaging of semiconductor devices for such applications as laser probing, TIVA/LIVA, OBIRCH, and photon emission timing analysis. A hybrid scanning optics configuration is disclosed to provide high resolution imaging over a small area along with low resolution imaging over a large area.

48 Claims, 10 Drawing Sheets

SCANNING OPTICAL SYSTEM

FIELD OF THE INVENTION

This invention relates to optical microscopy, and in particular to achieving increasingly high imaging resolution and high collection efficiency of an optical system used for integrated circuit probing.

BACKGROUND OF THE INVENTION

As integrated circuit geometries shrink, the resolution must be improved for optical systems which may be used in such applications as inspection systems and circuit probe and/or repair systems. Many probe systems used for complex circuitry having multiple metallization layers utilize backside probing and imaging. A description of a backside probing system including backside imaging is found in U.S. Pat. No. 6,518,571, issued Feb. 11, 2003. For backside imaging and probing through silicon, the transmission window of silicon combined with electro-optical effects in silicon restrict the useable optical wavelengths to the near infrared (NIR) region (900 nm to beyond 2000 nm). Thus, whereas for lithography applications optical resolution can be improved by moving to shorter wavelengths, for many probing applications the wavelengths are restricted and the optical resolution improvement cannot be achieved by this method. The most practical alternative for improving optical resolution for probing applications is to increase the numerical aperture (NA) of the objective lens used for focusing light onto the Device Under Test (DUT) and for collecting light from the DUT.

Prior methods for achieving high NA for imaging/probing systems have inherent drawbacks. One serious drawback is the high cost of high NA lenses (NA>1). A well-known type of high NA lens, the Solid Immersion Lens (SIL), tends to have a small field of view and is very difficult and costly to design with a reasonable field of view. It is also difficult to design a SIL that is apochromatic (color corrected over a range of wavelengths).

It would be a significant advance in optical systems for probe applications to provide a high NA, large field of view optical system which could be utilized for a wide range of applications such as: 1) optical probing applications, one example being laser probing applications, 2) photon emission timing analysis applications, and/or 3) applications such as TIVA/LIVA, (Thermally Induced Voltage Alteration/Light Induced Voltage Alteration), OBIRCH/OBIC (Optical Beam Induced Resistance Change/Optical Beam Induced Current), and RIL (Resistive Interconnection Localization) wherein the "image" is formed by monitoring either the DUT or a tester connected to the DUT, rather than being formed from the reflected laser light. It would be of further benefit to provide a hybridized method of combining traditional imaging with a low field of view lens, combined with imaging with a high NA, large field of view optical system in order to provide increased speed for the imaging operation.

SUMMARY OF THE INVENTION

It is therefore an object of this invention to provide a high NA, large field of view optical system which can be utilized for optical probing applications, for example laser probing applications.

It is a further object of this invention to provide a high NA, large field of view optical system which can be utilized for photon emission timing analysis;

It is a further object of this invention to provide a high NA, large field of view optical system which can be utilized for TIVA/LIVA, OBIRCH/OBIC, or RIL applications;

It is a further object of this invention to provide a hybridized method of combining traditional imaging with a low field of view lens, combined with imaging with a high NA, large field of view optical system in order to provide increased speed for the imaging operation;

It is a still further object to provide methods for prolonging the useful life of traditional imaging components when used in the aforementioned hybridized method.

It is a further object to provide a high NA, large field of view optical system which can be utilized for optical probing applications which is lower cost.

DETAILED DESCRIPTION OF THE INVENTION

Figure 1:
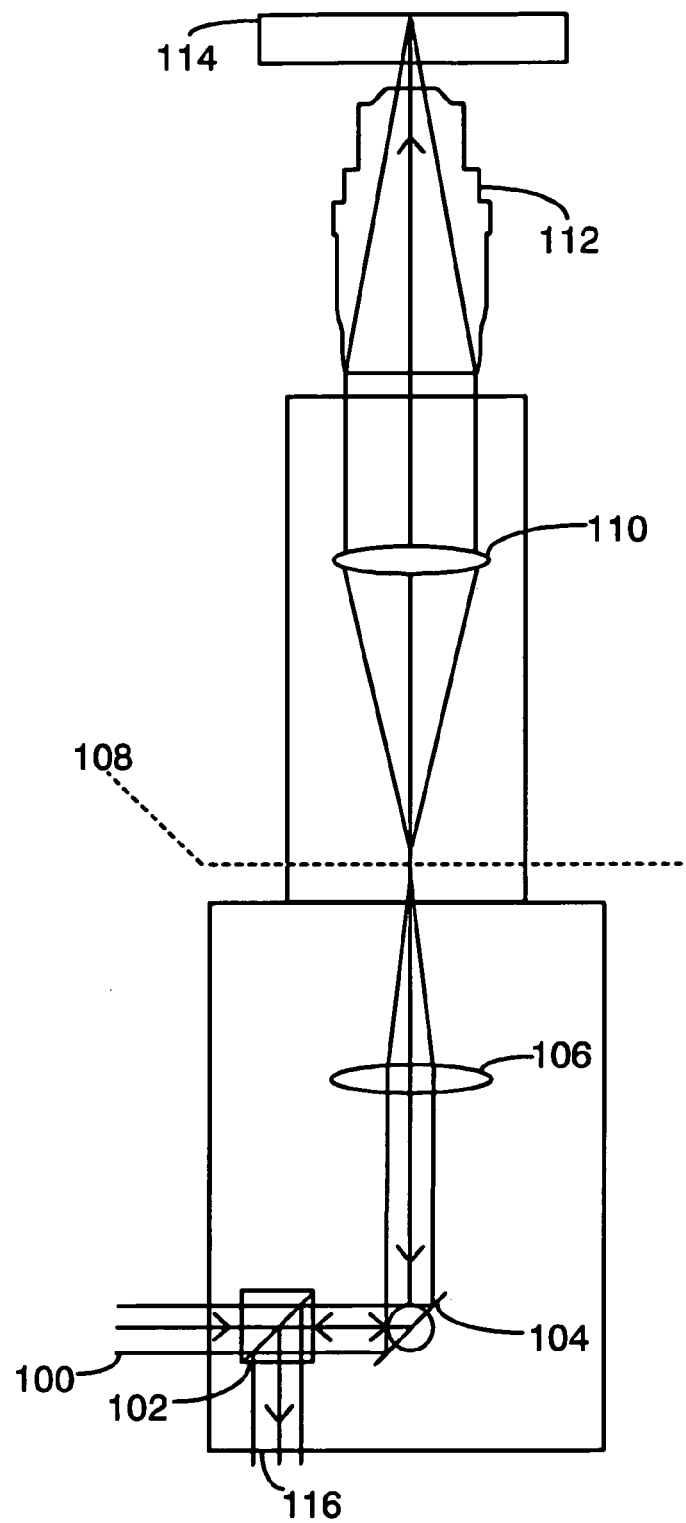
FIG. 1 illustrates the optical path of a conventional Laser Scanning Microscope.

FIG. 1 illustrates the optical path of a conventional Laser Scanning Microscope (LSM), an example of which is the LSM-1064 manufactured by Checkpoint Technologies. Incident, collimated light 100 from a laser source (which may be delivered from a fiber+fiber collimator) impinges on beamsplitter 102, which is used to separate incident light from reflected light. Beamsplitter 102 may be a polarizing beamsplitter used in conjunction with a quarter-wave plate to improve transmission efficiency. Light 100 impinges on galvo-mirrors 104, which are rotated to generate a raster scan pattern of the light beam incident on a sample. Generally, two galvo-mirrors are used, one for x-scan and another for y-scan. There are alternative means for generating a raster scan pattern, such as acousto-optic crystals, or tip-tilt piezo scanners. These methods are described in Corle, T. R. and G. S. Kino, *Confocal Scanning Optical Microscopy and Related Imaging Systems.* 1996, San Diego: Academic Press, which is hereby incorporated by reference in its entirety.

F-theta lens 106 converts the angular scan produced by galvo-mirrors 104 into an x-y raster scan pattern at intermediate image plane 108. Objective lens 112 focuses incident light onto DUT 114 and receives reflected light 116. Tube lens 110 in combination with objective lens 112 projects an image of the DUT onto imtermediate image plane 108. Examples of objective lenses which may be used, not to be considered a comprehensive list, are Hamamatsu A3717 100×, OPTEM liquid immersion lens 100×, Mitutoyo M Plan NIR series of lenses (5×, 10×, 20×, 50×, 100×), or other lenses made by vendors such as Nikon, Olympus, or Zeiss. Solid immersion lenses may also be used. Light retro-reflected by the DUT is re-collimated by the objective lens, then is split off at beam splitter 102 and may be coupled into a fiber optic cable using a fiber coupling lens and delivered to a photodetector. Imaging is performed by raster scanning the laser beam across the region of interest on the DUT, using galvo-mirrors 104, and collecting the reflected light. The image is generated digitally by displaying the gray-coded reflected light intensity vs. the galvo-mirror positions.

Figure 2:
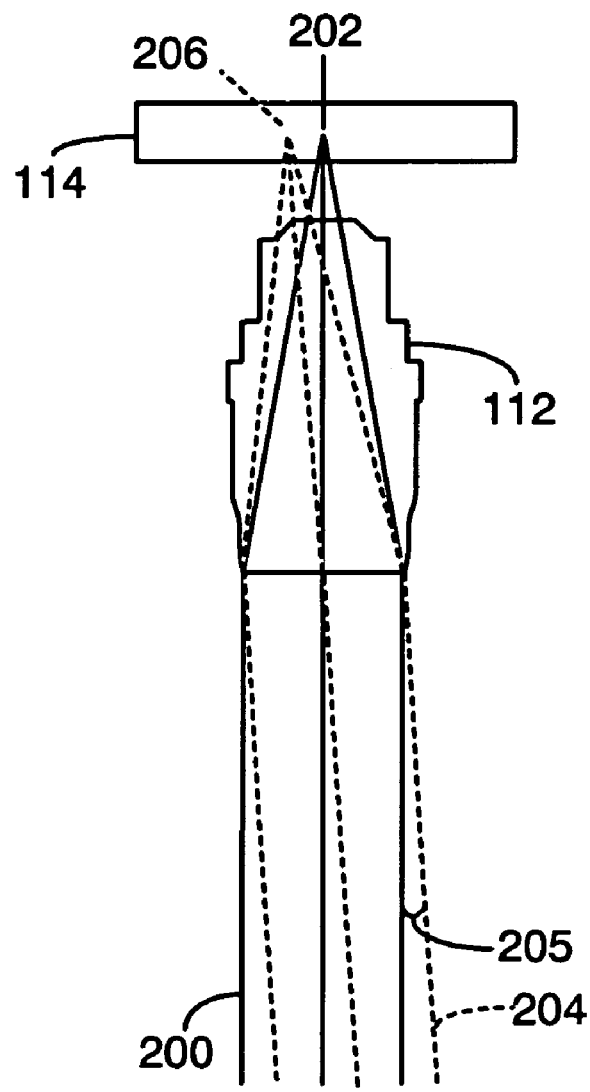
FIG. 2 is a close-up view of the objective lens-DUT region for the conventional LSM.

FIG. 2 is a close-up view of the objective lens-DUT region for the conventional LSM, showing two beam paths through objective lens 112. Beam 200 is un-deflected, i.e., on-axis, and impinges on DUT 114 at point 202. Beam 204 has been deflected by the raster-scan mechanism such as the galvo-mirrors, at an angle 205 from the on-axis beam, and impinges on DUT at point 206. The field of view is determined by the area encompassed on the DUT by the raster scan, i.e., a larger maximum beam deflection angle 205 results in a larger field-of-view.

Conventional optical microscopes, whether they are LSM-based or based on a flood illumination light source with a focal plane array detector such as a CCD camera, require that objective lens 112 be well corrected for off-axis light. An example of distortion which occurs, even over a relatively small field of view of the image, with solid immersion lenses that are not well corrected, is shown in "*High Spatial Resolution Subsurface Microscopy*", S. B. Ippolito, B. B. Goldberg, and M. S. Unlu, *Applied Physics Letters*, 78 (26) pp 4071–3, 2001. Significant distortion is apparent at the edges of the images. The images in this reference are taken at a single wavelength, so the additional distortion associated with a range of wavelengths are not apparent here. However, for such applications as photon emission timing analysis, the emission is broad band (1250 nm to 1750 nm, by way of example). Therefore, for this application, apochromatic optics (optics corrected over a wide range of wavelengths) are required. Correcting the optics requires additional optical elements in the lens system. The wider the angle required, for a larger field-of-view, the more difficult the corrections become. These additional corrective lenses, in general, make the objective lens 112 longer, wider, heavier, more expensive, and reduce the transmission of light through the lens. Requiring the lens to be apochromatic further increases the difficulty of the task.

A method of simplifying the optics while maintaining a large effective field of view for the image is described by Minski in U.S. Pat. No. 3,013,467, issued Dec. 19, 1961. In this method, the DUT is scanned in a raster pattern and only on-axis illumination/collection is used in the optics. By mapping light intensity to the DUT position, an image is generated. This method would reduce the demands on the optics; for example, field-of-view of the objective lens could be essentially zero. The method described in Minski is not applicable to probe systems, since in probe systems the DUT is generally connected to a stationary test head and cannot be easily scanned.

Figure 3A:
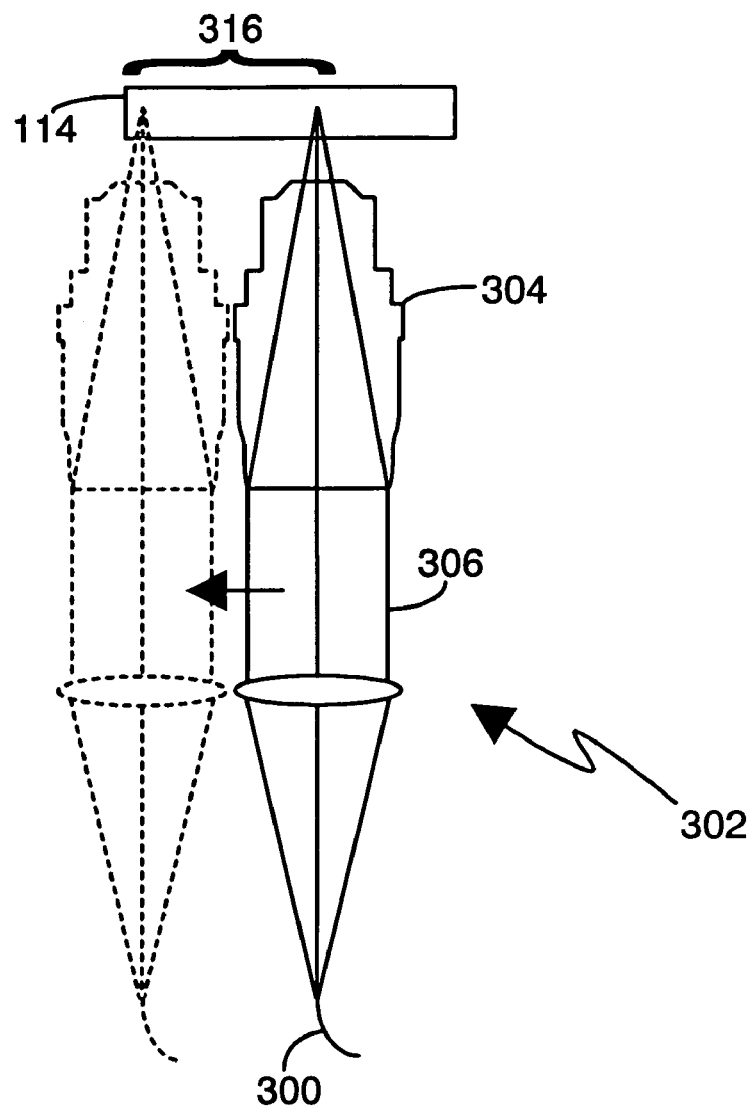
FIG. 3a illustrates a scanned optical system.

U.S. Pat. No. 6,462,814 by William Lo, issued Oct. 8, 2002, describes a scanning microscope system designed to provide a small size, lightweight, portable beam delivery and imaging subsystem which can be mounted quickly and easily to the test head of an Automated Test Equipment (ATE) system, while being decoupled from sources of vibrational noise. This system, illustrated in FIG. 3a, is suited to probe systems. Lo describes an optical probe system including a scanning microscope system wherein an objective lens 304 and tube-lens 306 combination is coupled to a fiber optic cable 300. The fiber delivers light to a sample (DUT) 114 and also collects the light reflected from the sample. The objective lens, tube lens, and fiber, i.e., the optical column 302, are mounted onto an X,Y,Z stage (not shown) which raster scans the optical column over the DUT in the xy plane, i.e., in the plane of the DUT surface, to form the image. The optical image is formed by the scanning of the optics across the field-of-view region 316, rather than varying the angle of the incident light with respect to the optical axis. This optical probe system and probing method as described in the issued patent is applicable to optical probing applications such as laser voltage probing applications where the reflected laser light is collected by the fiber optic cable. U.S. Pat. No. 6,462,814 is hereby incorporated by reference in its entirety.

By delivering light to the objective lens using fiber optic cable 300, collecting light reflected by the DUT 114 using a fiber and restricting the light to be on-axis, the microscope optics can be greatly simplified. The microscope optics can then be made sufficiently light weight that the optics can be scanned at a reasonable rate using an x,y,z stage, instead of scanning the DUT. The reflected light is separated from the incident light using a beamsplitter arrangement, which may be placed on the laser side of the fiber or elsewhere in the optical column.

Figure 3B:
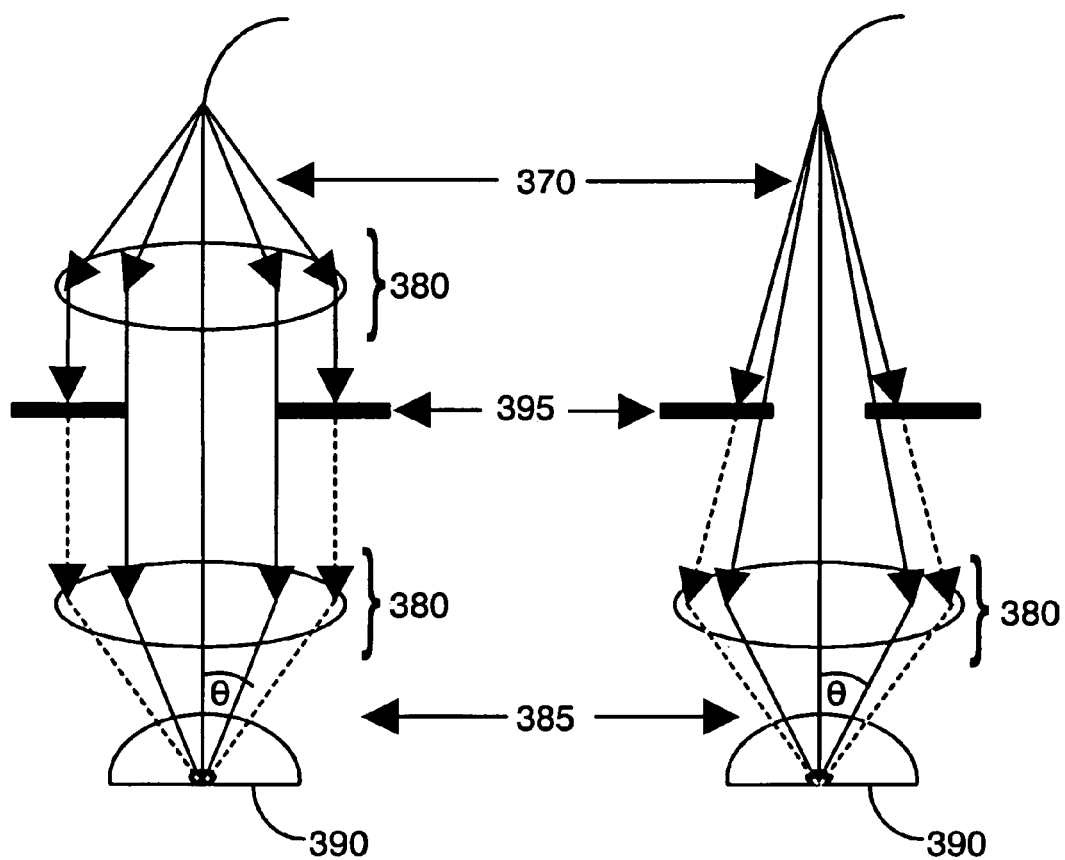
FIG. 3b illustrates the use of a non-collimated incoming light beam.

The present invention utilizes the method of scanning the optics so as to achieve a large field-of-view image, for optical probing applications such as laser probing applications. A further benefit is lowered costs for the optical column. The incoming light is not required to be highly collimated when entering the optic column, since the light delivery system may include lenses which focus or collimate the incoming light. FIG. 3b illustrates how diverging incoming light beam 370 can be transmitted through lens groups 380 to form converging light beam 385 which converges at sample surface 390. The present invention is also applicable to applications which do not form the image from reflected light, but rather by monitoring the DUT or tester response as the beam is raster scanned across it. Examples of such applications are TIVA/LIVA, OBIRCH/OBIC, and soft defect localization methods such as RIL and Thermal Laser Stimulation (TLS). TIVA and LIVA are described in U.S. Pat. No. 6,078,183, issued Jun. 20, 2000, and in U.S. Pat. No. 5,430,305 issued on Jul. 4, 1995. OBIRCH is described in U.S. Pat. No. 5,804,980 issued on Sep. 8, 1998. RIL is described in: Cole, E. I., Jr., et al. *Resistive Interconnect Localization*. in *International Symposium for Testing and Failure Analysis (ISTFA)*. 2001. All of these references are hereby incorporated by reference in their entireties.

In all of these applications, having a large field of view is desirable so as to effectively locate and isolate a defect. (In this context, the term "field of view" is used as applied to the incident light beam, to describe the region where the incident light is well focused on the sample, and not substantially degraded compared to the central beam region). There are large field of view (e.g., 1× lenses) commercially available, but they are not optimized for NIR wavelengths. In addition, numerical aperture is small (0.025 by way of example), yielding poor image resolution and large laser spot size. Since laser power density is important for these applications, having a large spot size would require more laser power.

A scanning lens microscope system, as proposed herein, could solve these problems since it de-couples field-of-view from the optical power requirements and NA of the lens. For example, a NIR 20× lens having NA=0.4 and FOV of about 800×800 microns could be used for an arbitrarily large field-of-view which is only limited by a) the x,y stage travel of the system, and b) the throughput requirements, since scanning over a larger field of view takes longer time. The inventive apparatus provides for a sufficiently large scan range to provide a FOV larger than is achievable using stationary corrected lenses, for lenses with high NA up to about 3.0. If the scanned optical system is not used, FOV generally decreases as lens power and NA increases. For example, an 0.8× lens having low NA, i.e. less than 0.025, has a well corrected FOV of about 20×20 mm. A 100× lens such as the Hamamatsu A3717 with an NA of about 0.85 has a well corrected field of view of about 160 microns×160 microns. Silicon solid immersion lenses (SIL) may have a diffraction limited NA close to 3.0, although in operation the NA of 3.0 is often degraded to values closer to 2.5 due to difficulty in making contact between the SIL and the sample. A 3.0 NA SIL would typically have a power of 350× and a field of view about 3.5 times smaller than the Hamamatsu lens, i.e., about 45 microns×45 microns. Even with extraordinary improvements such as custom lenses and microscopes, prior methods using SIL without scanning optics have not been able to achieve a FOV as high as 100×100 microns. However, by using the inventive method and apparatus, i.e., by providing a lightweight optical column and scanning it with a stage having a sufficiently large travel, the field of view of the SIL can be increased to a value substantially greater than 100×100 microns, while maintaining a NA (and therefore resolution) much greater than the Hamamatsu lens. Minimizing the weight of the optical column to be scanned is critical, for several reasons. The stages with highest resolution and accuracy, but having sufficiently large travel distance, have low load capacities. Additional factors which necessitate light weight scanned optical columns include the dependence of resonant frequency on the weight. The heavier the column, the lower the resonant frequency, which makes the system more vulnerable to such low frequency noise as acoustical or electrical noise. A preferred embodiment of the present invention utilizes a piezo flexture stage having a 200 micron travel in x and y. Some representative stages, with their scan rates and load capacities, are described in Table 1.

A combination stage may be used, wherein a fine stage with a small scan range is mounted on a coarse stage with a large scan range. This can be employed in two ways: a coarse stage with a large scan range but slow scan speed can be utilized to perform whole-die imaging if fast throughput is not critical. (Since the stage is stopped after each row of a raster scan, the

TABLE 1

CHARACTERISTICS OF STAGES

Figure 4:
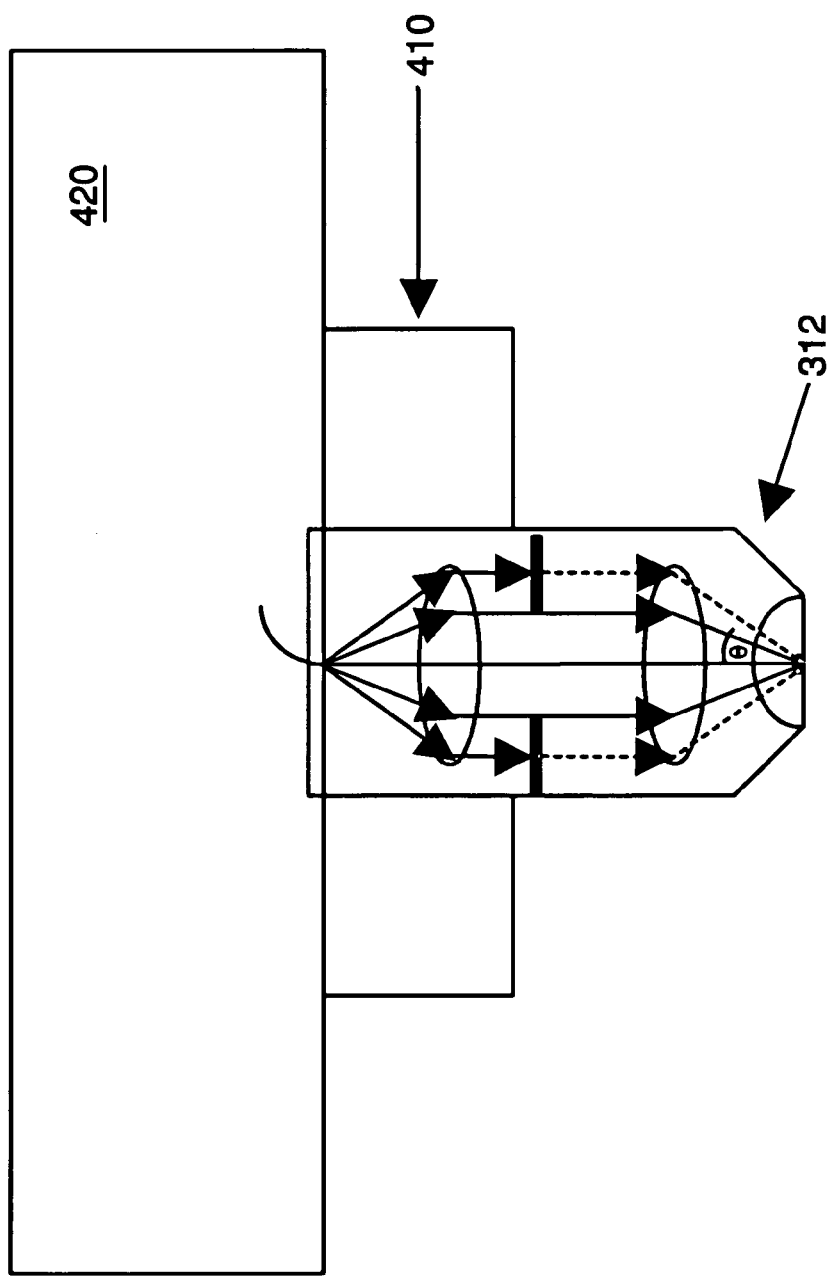
FIG. 4 illustrates a combination stage.

| Model No. | Travel distance | Load Capacity | Scan rate | Comments |
|---|---|---|---|---|
| Polytech PI P-527.3CL PI P-527.3CD | 200 × 200 microns (xy) 20 microns (z) | 2500 gram with 110 Hz resonant frequency: 500 gram with 190 Hz resonant frequency | 40–50 Hz at 500 gram load | Piezo-stages: Scan speed should be limited to about ¼ of resonant frequency High resolution and accuracy, in nanometer range. Very compact |
| Polytech PI V-102.2L | 5 mm (xy) z-stage not built in | Less than 100 grams | Less than 5 Hz | Voice coil stage Can add P-720.00 PIFOC positioner for 100 microns z-travel. Compact. |
| Polytech PI M-511.DG PI M-511.2S | 102 mm (single axis) | 100 Kg | For 5 × 5 mm FOV, 1 Hz (.DG) 5 Hz (.2S) (ignoring turn-around time). | Doubling FOV yields half scan rate Can use two stages for x and y, add PIFOC for z .1 micron resolution. Accuracy 1 micron. Each stage weighs 5.1 kg |
| Polytech PI M-605.1DD PI M-605.2DD | 25 mm (.1DD) 50 mm (.2DD) single axis for x, y, z | 30 Kg | For 5 × 5 mm FOV, 10 Hz (ignoring turn-around time) | Need to stack 3 stages together for x, y, z .1 micron res., .2 micron accuracy | stopping time and start-up time, i.e., turn-around time, of a heavy coarse stage can be considerable.) An example of a dual-stage configuration is to use a Polytech 3× PI M-605.2DD (stacked for X,Y,Z) together with 1× P-527.3CL. This configuration would give faster scanning over 200 micron range with greater accuracy/resolution, and slower scanning over 50 mm with decreased accuracy/resolution. Alternately, a large-range, moderate speed coarse stage could be used to move the optical column to approximately the desired location to do high resolution imaging using the fine stage. Such a coarse stage could be manual and lightweight. An example of a possible combination stage is illustrated in FIG. 4. Optical column 312 is mounted on fine stage 410, e.g., Polytech 1× P-527.3CL, which in turn is mounted on stacked coarse stage 420, e.g., Polytech 3× PI M-605.2DD (stacked for X,Y,Z).

An embodiment of the present invention extends the method of scanning the optics to achieve a large field-of-view image to photon emission timing analysis applications, which are described in: 1) Lo, W., et al. *Next-Generation Optical Probing Tools for Design Debug of High Speed Integrated Circuits*. in *International Symposium for Testing and Failure Analysis (ISTFA)*. 2002; and 2) Somani, S., et al., *A New Photon Detector for Device Analysis: Superconducting Single Photon Detector Based On a Hot Electron Effect*. J. Vac. Sci. Technol. B., 2001. 19(6): p. 2766–9. Both of these references are hereby incorporated by reference in their entireties.

Figure 5:
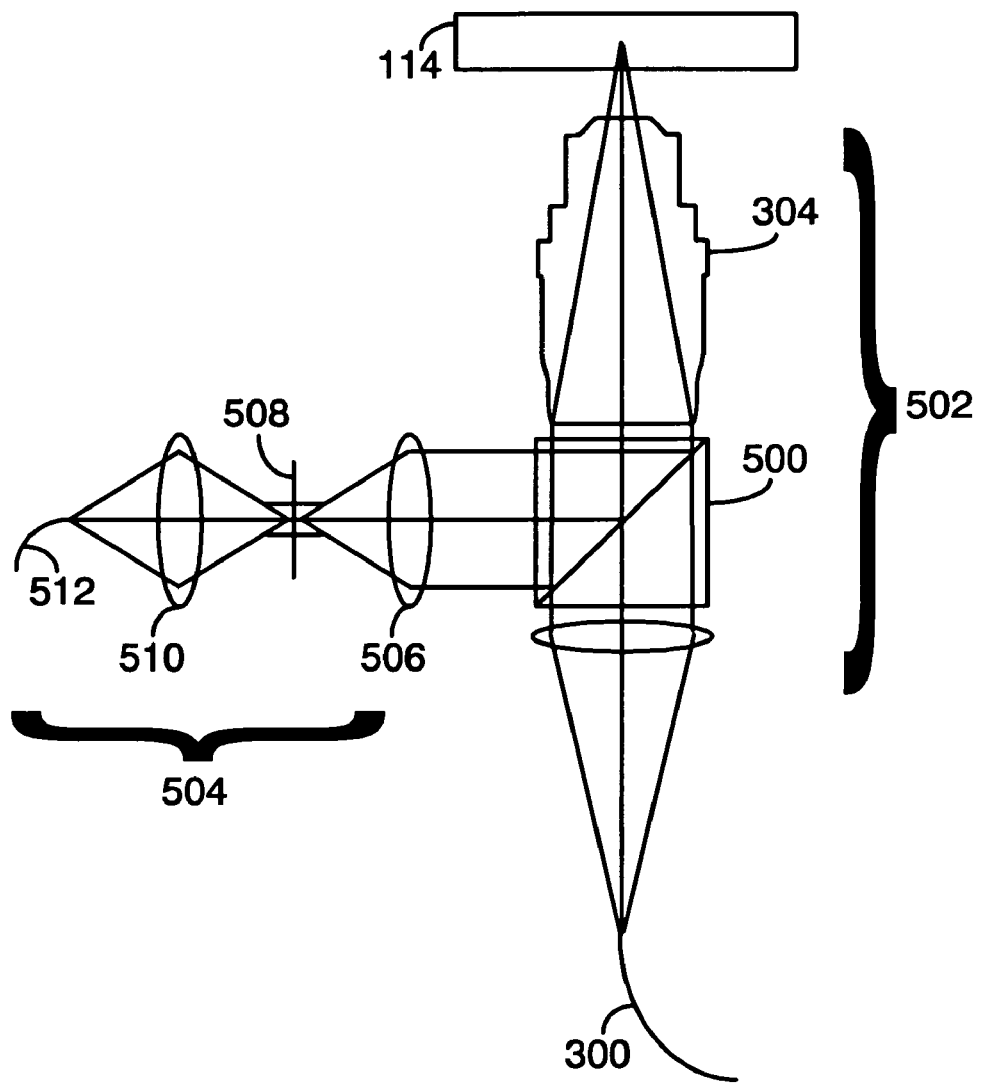
FIG. 5 illustrates a method and apparatus for scanning the optics to achieve a large field-of-view image for photon emission timing analysis applications.

This embodiment is illustrated in FIG. 5. Dichroic beamsplitter 500 is inserted into optical column 502, to separate the imaging laser wavelength from the photon emission wavelengths as efficiently as possible. In the embodiment as shown in FIG. 5, beamsplitter 500 ideally has the property that it transmits the imaging laser wavelength and reflects all other wavelengths. An alternate embodiment, which would require some re-arrangement of optics, would comprise a beamsplitter which reflected at the imaging laser wavelength and transmitted at all other wavelengths. Photons emitted by the DUT 114 are diverted into photon emission timing port 504 which consists of: focusing lens 506, selectable area aperture 508, fiber coupling lens 510, and multi-mode fiber optic cable 512. Collecting the emission with a multi-mode fiber in place of the single mode fiber 300 used for imaging improves the collection efficiency and enables photons to be collected from a larger region. Selectable Area Aperture (SAA) 508 enables the region in the DUT over which emission is collected to be restricted, in order to minimize signal contamination/cross talk. To form an image, all of the optics are scanned across the DUT. It is expected that, using photonic crystal fibers, it will be possible to use a single fiber to both act as a single-mode fiber for delivering the imaging laser beam, and to act as a multimode fiber for collecting the emitted photons. The imaging beam and emitted photons could then be separated after passing through the fiber, which would simplify the optics. The SAA would still need to be located in the scanning portion of the optics.

The present invention can be implemented using a variety of types of objective lenses. Non-immersion objectives, such as the Hamamatsu A3717, can be used, as well as solid or liquid immersion objectives. Immersion lenses, particularly SIL's, provide a very high NA and therefore have great potential benefit in the use of the scanning optical system for the resolution of ever smaller geometries on the DUT. Commercially available objective lenses are generally corrected to enlarge the FOV, using additional optical components which add weight. For application to the present invention, no such FOV enhancement is necessary, therefore custom made lightweight, compact lenses with optimal NA and minimal FOV can be designed.

Figure 6A:
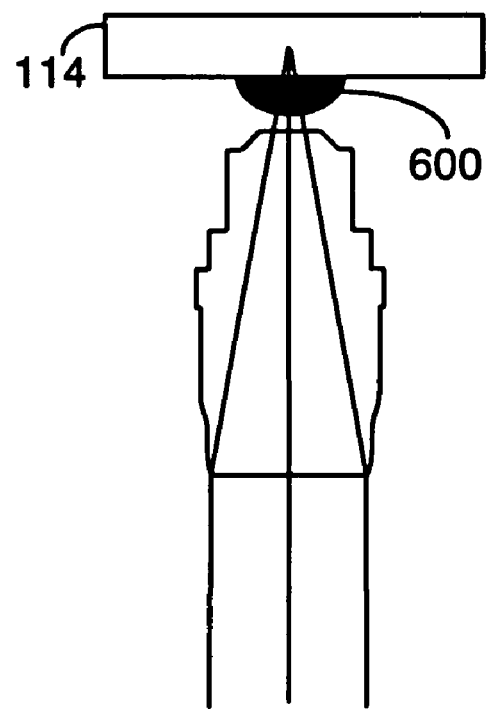
FIG. 6a illustrates SIL geometry, wherein the SIL is in intimate contact with the DUT.

One potentially serious issue with using a SIL in a scanning optical system is the possibility of damage to the SIL or to the DUT during the scanning. The final lens element in the SIL must be in intimate contact with the DUT (any gap must be much smaller than 1 micron). FIG. 6a illustrates the SIL geometry, wherein SIL 600 has a back surface which is substantially semispherical with a radius of curvature, and has a front face having a fairly large area, which has a radius of curvature much larger than that of the back surface, and is in intimate contact with DUT 114. A known method for minimizing damage to a lens is a "duck and cover" scheme which has been implemented in the IDS2500I probe system manufactured by NPTest, which utilizes a conventional LSM and a short-distance liquid immersion lens. When the optical system is moved relative to the sample, e.g., for locating the desired spot on the DUT to be imaged, the lens is retracted from the sample before moving. This method could be utilized for an SIL application in a scanning optical system as described herein, by: 1) retracting the SIL in z, i.e., perpendicular to the sample surface, 2) moving the optical column laterally, then; 3) moving the SIL back in z to contact the sample. This process would be repeated for each pixel in the image, which would be a time-consuming process if the z-stage were utilized to move the lens.

Figure 6B:
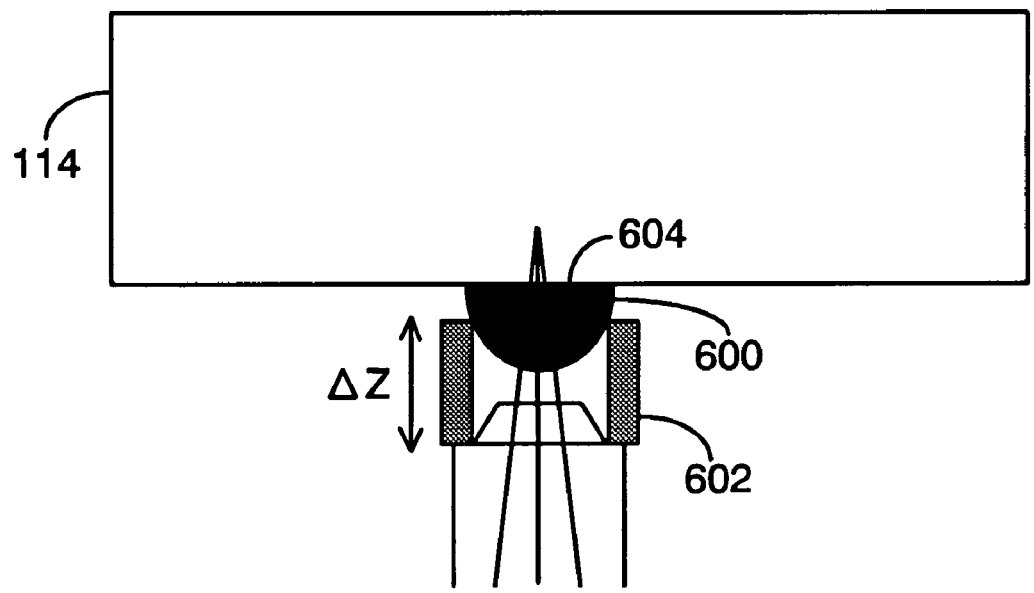
FIG. 6b illustrates an embodiment of this invention wherein an SIL is mounted to a piezo-electric crystal.

An embodiment of the present invention, which addresses the issue of damage to the SIL or DUT during scanning, employs a piezo-electric crystal to oscillate the final lens element in z by a small amount, 100 nm oscillation amplitude by way of example. The oscillation would reduce or eliminate lateral shearing effects and thereby reduce damage. This embodiment is illustrated in FIG. 6b, wherein SIL 600 is mounted to piezo-electric crystal 602. With a sufficiently small oscillation amplitude, it is expected that the gap between the final lens element and the DUT would remain small enough that the SIL performance would not be substantially affected, although effects on focus are expected and would need to be investigated. Oscillation frequency may be as high as several kHz. Oscillation amplitude can be monitored as a method of sensing the strength of the lens/DUT interactions (e.g., electromagnetic or shear force interactions), so as to determine the proximity of the lens to the sample. (For determining shear force interactions, the piezo-electric crystal may utilize oscillations in the xy plane). This technique has application in the case of a sample which is warped or tilted with respect to the xy plane defined by the stage travel. Alternatively, the piezo-electric crystal may be used to rapidly retract the SIL by a larger amount, about 1 micron or more, as the SIL is moved to the next pixel. This retraction method is considerably faster than retracting the entire optical column using the z-stage.

A related sub-embodiment which may be used alone or in combination with the oscillating final lens element employs the application of a thin wear-resistant coating 604 to the lens surface and/or the DUT. The film is either comprised of a material with a high index of refraction (greater than or equal to that of silicon for a silicon SIL) and is NIR transparent, or else has a thickness much smaller than the wavelength of light used. Examples of materials which may be used include: 1) NIR-transparent diamond film, 2) diamond-like carbon film, 3) titanium nitride, 4) aluminum nitride, 5) silicon carbide, and 6) micro-nano spheres such as Bucky-balls, i.e., carbon-60 molecules with a diameter of about 3 nanometers, which may be deposited on the lens and/or the DUT.

Figure 7A:
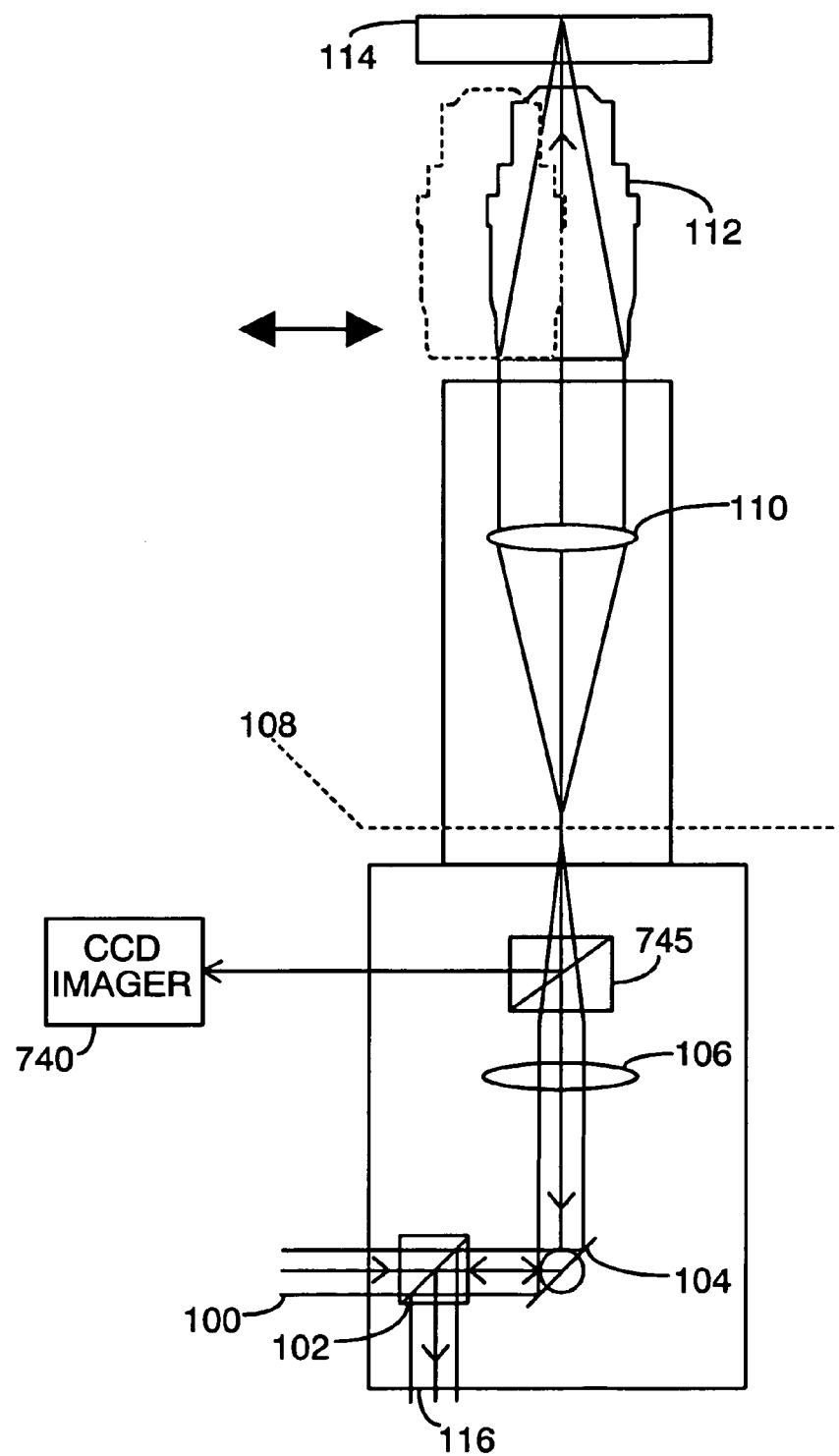
FIG. 7a illustrates a hybrid scanning scheme utilizing raster scanning.

An embodiment of this invention employs a hybrid scanning lens scheme, which incorporates both the scanned optical column as described herein for high resolution imaging, and low resolution imaging such as a) CCD imaging 740, or b) the raster scanning used in conventional LSM's, for coarse navigation. This embodiment, showing both the optional raster scanning and the optional CCD, is illustrated in FIG. 7a. A lens is used which may not have a large, corrected field-of-view. For the raster scanning method of coarse navigation, normal microscope imaging is used in which the LSM scans the laser beam 100 in a raster pattern. Off-axis imaging will be degraded, but is sufficient for coarse navigational purposes. If CCD imaging is used, the reflected beam is diverted to CCD imager 740 by beamsplitter 45. When a high quality image is required to precisely identify or examine features, the LSM scan mirror 104 is stopped in the center of its scan, corresponding to on-axis illumination of the lens, and the objective lens 112 is scanned in x and y across the DUT. As long as the collimated diameter of the beam filling the objective lens is much greater than the x,y scan range of the lens, the image quality is not expected to be degraded due to misalignment of the objective lens.

Figure 7B:
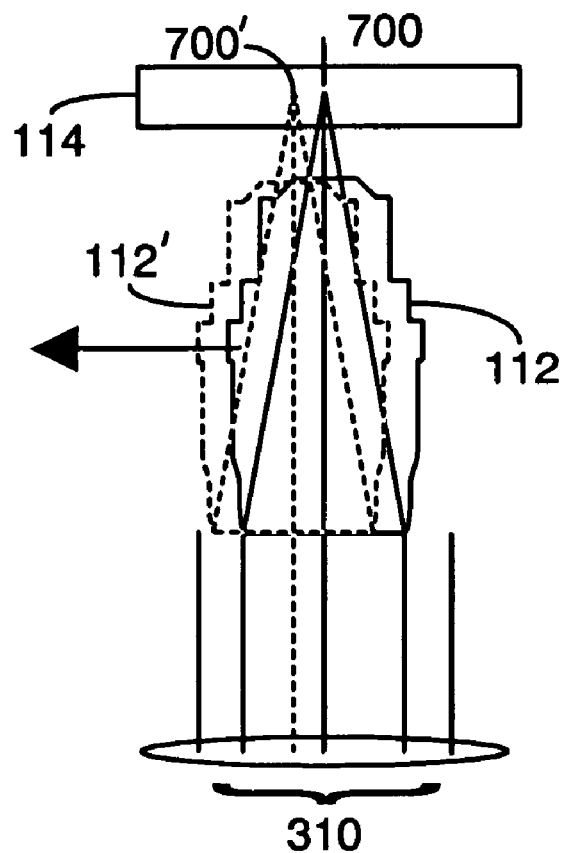
FIG. 7b illustrates the embodiment of FIG. 6a, enlarged to show the objective lens region.

FIG. 7b illustrates the embodiment of FIG. 7a, enlarged to show the objective lens region. Following the coarse navigation which utilizes the raster scanning of the galvo-mirrors, the galvo-mirror scanning is suspended, with beam 310 fixed so as to be on-axis with the axis of objective lens 112. In this region of the objective lens, aberrations are well corrected. Beam 310 overfills, i.e., is substantially wider than, objective lens 112, so that small movements of lens 112 with respect to beam 310 do not result in additional, significant aberrations. Objective lens 112 is scanned in x,y with respect to DUT 114, as indicated by offset lens (dotted line) 112'. As the lens moves, focused point 700 moves (to first order) with the optic axis of the lens, to offset focused point 700'. This method allows lens design to be greatly simplified since the lens only needs to be well corrected for on-axis points. It also enables the field of view to be increased without distorting the image. The hybrid scanning lens method as disclosed herein increases throughput by utilizing fast raster scanning for coarse navigation, and utilizing the relatively slower scanning of the optical column only in those regions where high resolution is required. The hybrid scanning lens method also minimizes the amount of time during which a lens such as an SIL would be translated across the DUT, thereby minimizing potential for lens damage.

An alternative hybrid embodiment scans the entire optical column for the high resolution portion of the imaging, rather than scanning just the objective lens.

Coarse raster scanning, coupled with small laser beam spot size, has the potential for skipping over small or narrow features if the successive scan lines are too far apart. The spot size (full width half maximum) is given by $0.5\lambda/NA$. For example, for the 0.85 NA Hamamatsu lens using light with wavelength of 1.064 micron, spot size is 0.63 micron, whereas for the SIL with NA of 3.0 using the same light, the spot size is 0.18 micron. In that case, if the raster scan lines are substantially further apart than about 0.36 micron, small features may be skipped over. This problem can be overcome by artificially restricting the NA of the incident laser beam's objective lens, thereby degrading, i.e., increasing, the spot size. One way to achieve this restriction of the NA is to insert an aperture 395 (see FIG. 3*b*) into the light path, e.g., into the collimated beam portion, during the coarse navigation, or to utilize a variable aperture. An additional benefit from restricting the NA is an increase in depth of focus.

The inventive method and apparatus disclosed herein provides for high resolution optical imaging with a large field of view, without the need for complicated optics. This technique can be applied, not only to integrated circuit probing, but to any laser imaging applications, such as imaging of biological samples.

It is not intended that the invention be restricted to the exact embodiments disclosed herein. It should be apparent to those skilled in the field that modifications may be made without departing from the inventive concept. For example, other types of objective lenses may be used, and other types of coarse imaging may be employed.

The scope of the invention should be construed in view of the claims.

I claim:

1. A scanned optical system for use in optical probing applications, said scanned optical system enabling high Numerical Aperture and large field-of-view, comprising:
   a light delivery system and focusing optics, said light delivery system and focusing optics forming an optical column with an optical axis;
   said light delivery system configured to deliver light from a light source to illuminate a sample (DUT) having a sample surface;
   said optical column being mounted on an xyz stage configured to scan the optical column across the DUT in the xy plane, said xy plane being parallel to said sample surface and z being perpendicular to said sample surface;
   a control system operable to move the xyz stage so as to scan the optical column across the DUT;
   said control system providing said xyz stage with a sufficiently large x-y scan range to provide said focusing optics with a field of view (FOV) of at least 100×100 microns for diffraction limited numerical aperture (NA) as high as 3.0;
   said light being directed in a light beam substantially parallel to said optical axis.

2. The scanned optical system of claim 1, wherein said optical column includes light collection optics, said x-y scan range being sufficiently large to provide said light collection optics with a field of view of at least 100×100 microns.

3. The scanned optical system of claim 2, wherein said light collection optics are imaging optics.

4. An optical probe system including the scanned optical system of claim 3, wherein said imaging optics form an image from reflected light from said DUT.

5. An optical probe system as in claim 4, wherein said light source is a laser having a narrow wavelength distribution centered on a wavelength value.

6. The optical probe system of claim 4, wherein said focusing optics and said imaging optics comprise an immersion lens.

7. The scanned optical system of claim 6, wherein said immersion lens is an SIL having a back surface with a first radius of curvature, and a front surface with a second radius of curvature proximal said DUT, said second radius of curvature being much larger than said first radius of curvature.

8. The optical probe system of claim 7, wherein said SIL has a NA of at least 2.5.

9. A scanned optical system as in claim 2, wherein;
   said light source is a laser having a narrow wavelength distribution centered on a wavelength value;
   said optical column further includes a beamsplitter to separate reflected light at said laser wavelength value from photons emitted by the DUT; and
   said beamsplitter diverts said photons emitted by said DUT into a photon emission timing port extending from said optical column.

10. An optical probe system including the scanned optical system of claim 9, said optical probe system providing photon emission timing analysis.

11. The scanned optical system of claim 9, wherein said focusing optics and said light collection optics comprise an immersion lens.

12. The scanned optical system of claim 11, wherein said immersion lens is an SIL having a back surface with a first radius of curvature, and a front surface with a second radius of curvature proximal said DUT, said second radius of curvature being much larger than said first radius of curvature.

13. The scanned optical system of claim 12, wherein said SIL has a NA of at least 2.5.

14. The scanned optical system of claim 3, wherein said focusing optics and said imaging optics comprise an immersion lens.

15. The scanned optical system of claim 14, wherein said immersion lens is an SIL having a back surface with a first radius of curvature, and a front surface with a second radius of curvature proximal said DUT, said second radius of curvature being much larger than said first radius of curvature.

16. The scanned optical system of claim 15, where said SIL has a NA of at least 2.5.

17. An optical probe system including the scanned optical system of claim 1.

18. An optical probe system for optically probing an electrical device on a DUT while operating the device under control of a tester, said tester operable to apply a sequence of test vectors to said device;

said optical probe system including the optical system of claim 1;
said optical probe system operable to form an image from monitoring the response from one of the group consisting of: the DUT and the tester; to said sequence of test vectors.

19. The optical probe system of claim 18, said system being selected from the group consisting of; a TIVA system, a LIVA system, an OBIRCH system, and an OBIC system.

20. The optical probe system of claim 18, said optical probe system being a soft defect localization system.

21. The optical probe system of claim 20, wherein said soft defect localization system is selected from the group consisting of: a RIL system and a TLS system.

22. The optical probe system of claim 18, wherein said focusing optics comprise an immersion lens.

23. The scanned optical system of claim 22, wherein said immersion lens is an SIL having a back surface with a first radius of curvature, and a front surface with a second radius of curvature proximal said DUT, said second radius of curvature being much larger than said first radius of curvature.

24. The optical probe system of claim 23, wherein said SIL has a NA of at least 2.5.

25. The scanned optical system of claim 1, wherein said focusing optics comprises an immersion lens.

26. The scanned optical system of claim 25, wherein said immersion lens is an SIL having a back surface with a first radius of curvature, and a front surface with a second radius of curvature proximal said DUT, said second radius of curvature being much larger than said first radius of curvature.

27. The scanned optical system of claim 26, wherein said SIL has a NA of at least 2.5.

28. The scanned optical system of claim 26, further including means for retracting said SIL from said sample surface while scanning said optical column across said DUT.

29. The scanned optical system of claim 28, wherein said means for retracting said SIL from said sample surface comprises said SIL being mounted on a piezo-electric crystal, said piezo-electric crystal being operable so as to oscillate said SIL in the z-direction.

30. The scanned optical system of claim 28, wherein said means for retracting said SIL from said sample surface includes said SIL being mounted on a piezo-electric crystal, said piezo-electric crystal being operable so as to oscillate said SIL in the xy plane.

31. The scanned optical system of claim 28, wherein said means for retracting said SIL from said sample surface comprises said z-stage moving said SIL.

32. The scanned optical system of claim 26, wherein a wear-resistant coating having a thickness is provided for at least one of: said SIL and said sample surface.

33. The scanned optical system of claim 32, wherein said wear-resistant coating is provided for said SIL.

34. The scanned optical system of claim 33 wherein said wear-resistant coating has index of refraction higher than that of Si, said wear-resistant coating being NIR transparent.

35. The scanned optical system of claim 33 wherein said thickness of said wear-resistant coating is smaller than the wavelength of said light.

36. The scanned optical system of claim 33 wherein said wear resistant coating is comprised of a material selected from the group consisting of:
NIR-transparent diamond film, diamond-like carbon film, titanium nitride, aluminum nitride, silicon carbide, and Bucky-balls.

37. The scanned optical system of claim 1, wherein said xyz stage comprises;
a low resolution stage having a large scan range; and
a high resolution stage having a small scan range mounted onto said low resolution stage.

38. A hybrid scanning lens optical system, including;
a light delivery system and focusing optics, said light delivery system and focusing optics forming an optical column with an optical axis;
said light delivery system configured to deliver light from a light source, said light forming a beam having a beam cross-sectional area, said beam illuminating a sample (DUT) having a sample surface;
means for scanning said focusing optics across the DUT in a scan region, said focusing optics being scanned in the xy plane, said xy plane being parallel to said sample surface and z being perpendicular to said sample surface;
said scanning of said focusing optics providing high resolution imaging within said scan region; and
means for providing low resolution imaging across a large area of said DUT.

39. The hybrid scanning lens optical system of claim 38, wherein said means for providing low resolution imaging across said large area of said DUT comprises a CCD imager.

40. The hybrid scanning lens optical system of claim 38, wherein said means for providing low resolution imaging across said entire DUT comprises:
said focusing optics comprising an objective lens having a small field of view;
a rotatable scan mirror in said optical column for raster scanning said beam across said DUT; and
a controller for rotating said scan mirror to raster scan said beam.

41. The hybrid scanning lens optical system of claim 40, including means for restricting the NA of said objective lens during said raster scanning.

42. The hybrid scanning lens optical system of claim 41, wherein said means for restricting the NA of said objective lens comprises an aperture positioned in said light beam within said optical column.

43. The hybrid scanning lens optical system of claim 38, wherein means for scanning said focusing optics comprises;
a fine xy stage for scanning said objective lens within said beam cross-sectional area;
a controller for scanning said fine xy stage;
said optical column remaining fixed.

44. The hybrid scanning lens optical system of claim 38, wherein means for scanning said focusing optics comprises;
said optical column being mounted on an xyz stage configured to scan the optical column across the DUT in the xy plane, said xy plane being parallel to said sample surface and z being perpendicular to said sample surface;
a control system operable to move the xyz stage so as to scan the optical column across the DUT;
said control system providing said xyz stage with a sufficiently large x-y scan range to provide said focusing optics with a field of view (FOV) of at least 100×100 microns for effective numerical aperture (NA) as high as 3.0.

45. A method for optically probing an electrical device (DUT) comprising:
operating the device;
providing a light delivery system and focusing optics, said light delivery system and focusing optics forming an optical column with an optical axis;

said light delivery system configured to deliver light from a light source to illuminate a sample (DUT) having a sample surface;

said optical column being mounted on an xyz stage configured to scan the optical column across the DUT in the xy plane, said xy plane being parallel to said sample surface and z being perpendicular to said sample surface;

providing a control system operable to move the xyz stage so as to scan the optical column across the DUT;

scanning said optical column across said DUT with a sufficiently large x-y scan range to provide said focusing optics with a field of view (FOV) of at least 100×100 microns for effective numerical aperture (NA) as high as 3.0;

providing light to illuminate said sample and monitoring a response to said illumination with respect to the xy position of said stage.

46. The method of claim 45, wherein said monitoring a response to said illumination includes forming an image of said DUT with respect to the xy position of said stage.

47. The method of claim 46, wherein said monitoring a response to said illumination further includes:

probing an electrical device on a DUT while operating the device under control of a tester, said tester operable to apply a sequence of test vectors to said device; and monitoring the response from one of the group consisting of; the DUT and the tester; to said sequence of test vectors.

48. The method of claim 46, wherein said monitoring a response to said illumination further includes receiving reflected light from said DUT.

* * * * *